(12) United States Patent
Bobbitt et al.

(10) Patent No.: US 10,322,153 B2
(45) Date of Patent: Jun. 18, 2019

(54) ANTI-MICROBIAL SEAWEED EXTRACTS, COMPOSITIONS AND USES THEREOF

(71) Applicant: OCEANS LTD., St. John's (CA)

(72) Inventors: Judith Bobbitt, St. John's (CA); Anne Mathieu, St. John's (CA); Ahmed Zein, St. John's (CA)

(73) Assignee: OCEANS LTD., St. John's (CA)

( * ) Notice: Subject to any disclaimer, the term of this patent is extended or adjusted under 35 U.S.C. 154(b) by 0 days.

(21) Appl. No.: 15/528,372

(22) PCT Filed: Dec. 11, 2015

(86) PCT No.: PCT/CA2015/051310
§ 371 (c)(1),
(2) Date: May 19, 2017

(87) PCT Pub. No.: WO2016/090494
PCT Pub. Date: Jun. 16, 2016

(65) Prior Publication Data
US 2017/0360859 A1   Dec. 21, 2017

Related U.S. Application Data

(60) Provisional application No. 62/090,973, filed on Dec. 12, 2014.

(51) Int. Cl.
| | | |
|---|---|---|
| A61K 36/03 | (2006.01) | |
| A61Q 17/00 | (2006.01) | |
| A61Q 19/00 | (2006.01) | |
| A61Q 19/10 | (2006.01) | |
| A61K 8/9711 | (2017.01) | |

(Continued)

(52) U.S. Cl.
CPC .......... *A61K 36/03* (2013.01); *A61K 8/9711* (2017.08); *A61Q 17/005* (2013.01); *A61Q 19/00* (2013.01); *A61Q 19/10* (2013.01); *A61K 9/0046* (2013.01); *A61K 9/06* (2013.01); *A61K 9/08* (2013.01); *A61K 9/14* (2013.01); *A61K 2236/00* (2013.01); *A61K 2236/15* (2013.01); *A61K 2236/17* (2013.01); *A61K 2236/33* (2013.01)

(58) Field of Classification Search
CPC ...... A61K 36/03; G01N 33/535; G01N 21/77; G01N 33/543; C12Q 1/28
USPC .......... 422/52, 562; 435/7.1, 7.9, 7.93, 7.94, 435/7.95, 28, 287.7, 287.8; 436/518, 524, 436/541, 805, 810
See application file for complete search history.

(56) References Cited

U.S. PATENT DOCUMENTS

| | | | |
|---|---|---|---|
| 2011/0217249 A1* | 9/2011 | Dreher | ................ A61K 9/0014 424/59 |
| 2013/0266522 A1 | 10/2013 | Fagon et al. | |

FOREIGN PATENT DOCUMENTS

| | | |
|---|---|---|
| EP | 0870507 A1 | 10/1998 |
| FR | 2980698 A1 | 4/2013 |
| WO | 2011109469 A1 | 9/2011 |

OTHER PUBLICATIONS

Choi et al., J Environ Biol. May 2011;32(3):313-8.*

(Continued)

*Primary Examiner* — Jana A Hines
(74) *Attorney, Agent, or Firm* — Hovey Williams LLP

(57) ABSTRACT

The present invention provides a crude extract, fractions and sub-fractions from the seaweed *Fucus distichus* (FD), method of preparation and its use for inhibiting the growth of microbial cells, particularly bacteria causing acne or nosocomial infections such as MRSA in humans or MRSP in dogs.

11 Claims, 8 Drawing Sheets

(51) Int. Cl.
*A61K 9/00* (2006.01)
*A61K 9/06* (2006.01)
*A61K 9/08* (2006.01)
*A61K 9/14* (2006.01)

(56) References Cited

OTHER PUBLICATIONS

V. K. Morya & Jungeun Kim & Eun-Ki Kim, Applied Microbiology and Biotechnology, Nov. 17, 2011 (Nov. 17, 2011), vol. 93(1), pp. 71-182, ISSN 1432-0614 [ (Year: 2011).*

Amiguet et al., (Canadian Journal of Microbiology, 2011, 57(9): 745-749) (Year: 2011).*

Amiguet, et al., "Antibacterial properties of a glycolipid-rich extract and active principle from Nunavik collections of the macroalgae *Fucus evanescens* C. Agardh (Fucaceae)", NRC Research Press, Can. J. Microbriol, 2011, vol. 57, pp. 745-749.

Jewell, "Synthesis of Glycolipids inspired by Fucus distichus and Natural Product Isolation and Characterization of Euphorbia Iancifolia", Thesis submitted to the School of Graduate Stidies and Research University of Ottawa, Carleton Chemistry Institute, Sep. 2009, 295 pages.

Rosell, et al., "Fatty acids as antimicrobial substances in brown algae", Twelfth International Seaweed Symposium, Sep. 1987, Hydrobiologia, vol. 151/152, pp. 471-475.

Morya, et al., "Algal fucoidan: structural and size-dependent bioactivities and their perspectives", Applied Microbriol. Biotech., Jan. 2012, vol. 93, issue 1, pp. 71-82 (abstract attached).

International Search Report and Written Opinion in corresponding PCT Application Serial No. PCT/CA2015/051310, dated Feb. 4, 2016, 12 pages.

International Preliminary Report in corresponding PCT Application Serial No. PCT/CA2015/051310, dated Jan. 5, 2017, 12 pages.

Supplementary European Search Report in EP 15868215, dated Jun. 20, 2018.

Kellogg et al., "Phlorotannins from Alaskan Seaweed Inhibit Carbolytic Enzyme Activity," Mar. Drugs 2014, vol. 12, pp. 5277-5294.

Kellogg et al., "Chemical and in Vitro Assessment of Alaskan Coastal Vegetation Antioxidant Capacity," J. Agric. Food Chem., 2013, vol. 61, pp. 11025-11032.

Farvin et al., "Phenolic compounds and antioxidant activities of selected species of seaweeds from Danish coast," Food Chemistry, 2013, vol. 138, pp. 1670-1681.

* cited by examiner

ANTI-MICROBIAL SEAWEED EXTRACTS, COMPOSITIONS AND USES THEREOF

RELATED APPLICATIONS

This application is the National Stage of International Patent Application No. PCT/CA2015/051310, filed Dec. 11, 2015, which is hereby incorporated by reference in its entirety, and which claims priority to U.S. Provisional Patent Application No. 62/090,973, filed Dec. 12, 2014.

FIELD OF THE INVENTION

The present invention relates to extracts from the seaweed *Fucus distichus* (*FD*), method of preparation and use for inhibiting the growth of microorganisms such as bacteria.

BACKGROUND OF THE INVENTION

Acne vulgaris is a common cutaneous multifactorial disease spread worldwide and caused by hormonal, microbiological and immunological mechanisms. Acne is characterized by open and closed comedones (blackheads and whiteheads) and inflammatory lesions like papules, pustules and nodules. *Staphylococcus aureus, Staphylococcus epidermidis* and *Propionibacterium acnes* are the organisms which proliferate rapidly and cause development of acne. The severity of this skin disorder generally increases with age and time. People normally get affected by it with the onset of puberty affecting both physical & psychological levels and therefore may constitute a cause of concern for treating physicians.

Acne affects all age groups i.e. 85% of teenagers, about 8% in 25-34 year olds and 3% in 35-44 year olds. Although it is not a life threatening disease, it is a distressing skin condition which causes significant psychological disability. Moreover, teenagers or young adults often experience the development of scar and scarring may affect up to 95% of the patients having acne.

There is a large and expanding market for over-the-counter (OTC) medications against acne. The estimated annual worldwide expenditure on acne OTC medication is $100 millions. The long term treatment of the present synthetic drugs comprising antibiotics and chemotherapeutic agents either inhibit excess sebum production, follicular hyperkeratinisation disorders, cytokines, reactive oxygen species and proliferation of *P. acnes* within the follicle. These drugs are applied either topically or taken orally for the treatment of acne.

The therapeutic success in the treatment of acne is highly dependent on the regular application of topical agents over a prolonged period of time. However the disadvantages associated with the existing topical therapies defeat the purpose of the treatment and make it patient-noncompliant. Currently available treatment for acne is based on antibiotics and retinoids. The use of antibiotics have lot of limitations due to the development of resistance by bacteria and their untoward side effects, such as skin dryness, pruritis, burning sensation, erythema, occasional hyper pigmentation, local irritation and photosensitization reactions. Furthermore, retinoids are highly teratogenic.

Also, extracts from plants and specific compounds obtained from plant sources are often used in cosmetic and pharmaceutical compositions. European Patent Application Publication No. 0 870 507 describes a synergistic antibacterial composition that includes an extract of botanical materials and an essential oil. The essential oil is described as having anti-microbial activity, whereas the extract of botanical materials has significantly lower activity, or no anti-microbial activity, when used alone.

Therefore alternative treatments of acne using natural products must be studied and developed. This creates a great interest in development of a topical formulation containing natural extracts possessing antibacterial effect to treat acne such as the development of present invention.

Nosocomial infections are hospital-acquired infections (HAI) or healthcare-acquired infections whose development is favored by a hospital environment, such as one acquired by a patient during a hospital visit or one developing among hospital staff. In the United States, the Centers for Disease Control and Prevention estimated roughly 1.7 million hospital-associated infections, from all types of microorganisms (i.e. bacteria), combined, cause or contribute to 99,000 deaths each year. Nosocomial infections can cause severe pneumonia and infections of the urinary tract, bloodstream and other parts of the body. Many types are difficult to treat with antibiotics, and antibiotic resistance is spreading to Gram-negative bacteria that can infect people outside the hospital.

Methicillin-resistant *Staphylococcus aureus* (MRSA) is responsible for several difficult-to-treat infections in humans. MRSA is any strain of *Staphylococcus aureus* that has developed, through resistance to beta-lactam antibiotics, such as the penicillin-types (methicillin, dicloxacillin, oxacillin, etc.) and the cephalosporins. This resistance makes MRSA infection more difficult to treat with standard types of antibiotics and thus more dangerous.

MRSA is especially troublesome in hospitals, prisons, and nursing homes, where patients with open wounds, invasive devices, and weakened immune systems are at greater risk of nosocomial infection than the general public. MRSA began as a hospital-acquired infection, but has developed limited endemic status and is now sometimes community-acquired.

Dogs can be carriers of MRSA and may be otherwise perfectly healthy. This is referred to as colonization. Though dogs are not normally colonized with MRSA, they can be exposed to a person that is colonized or who has an active infection, and therefore can become infected or colonized as well.

*Staphylococcus intermedius* is a common species of bacteria found in rabbits and is called *Staphylococcus pseudintermedius* when found in dogs. A small percentage of animals may develop skin infections caused by methicillin-resistant—*Staphylococcus intermedius* (MRSI) or—*Staphylococcus pseudintermedius* (MRSP), both infections being difficult to get rid of, and often require aggressive topical therapies.

SUMMARY OF THE INVENTION

A main aspect intended to be addressed by the present invention is to provide a novel extract from the seaweed *Fucus distichus* (FD).

According to a further aspect, the present invention provides a composition comprising the extract as defined herein, in admixture with a physiologically acceptable excipient.

According to a further aspect, the present invention provides a method for inhibiting a microorganism comprising contacting said cell with a growth-inhibiting concentration of the extract or the composition as defined herein.

According to a further aspect, the present invention provides a method for treating a microbial infection in a mammal comprising administering a growth-inhibiting concentration of the extract of the composition as defined herein to the mammal.

According to a further aspect of the present invention, there is provided use of the extract as defined herein for inhibiting growth of microbial cells.

According to a further aspect of the present invention, there is provided use of the extract as defined herein for the manufacture of composition for treating a microbial infection in a mammal.

According to a further aspect, the present invention provides use of the composition as defined herein for the treatment of a microbial infection in a mammal. Particularly, the microbial infection is a bacterial infection or an antibiotic-resistant bacterial infection.

According to a further aspect of the use or the method, both as defined above, the bacterial infection may be selected from the group consisting of: *Staphylococcus aureus*, methicillin-resistant *Staphylococcus aureus* (MRSA), *Staphylococcus epidermidis*, *Propionibacterium acnes*, *Staphylococcus intermedius* (SI), methicillin-resistant *Staphylococcus intermedius* (MRSI), *Staphylococcus pseudintermedius* (SP) and methicillin-resistant *Staphylococcus pseudintermedius* (MRSP).

According to a further aspect, the present invention provides a method for obtaining an extract from *Fucus distichus* comprising the steps of: a) mixing material from seaweed *Fucus distichus* (FD) with a solvent to obtain a solvent:material mixture; and b) separating a solid fraction and a liquid fraction from said mixture, said liquid fraction forming the extract.

Detailed Description of the Invention

ABBREVIATIONS AND DEFINITIONS

Abbreviations

Figure 1:
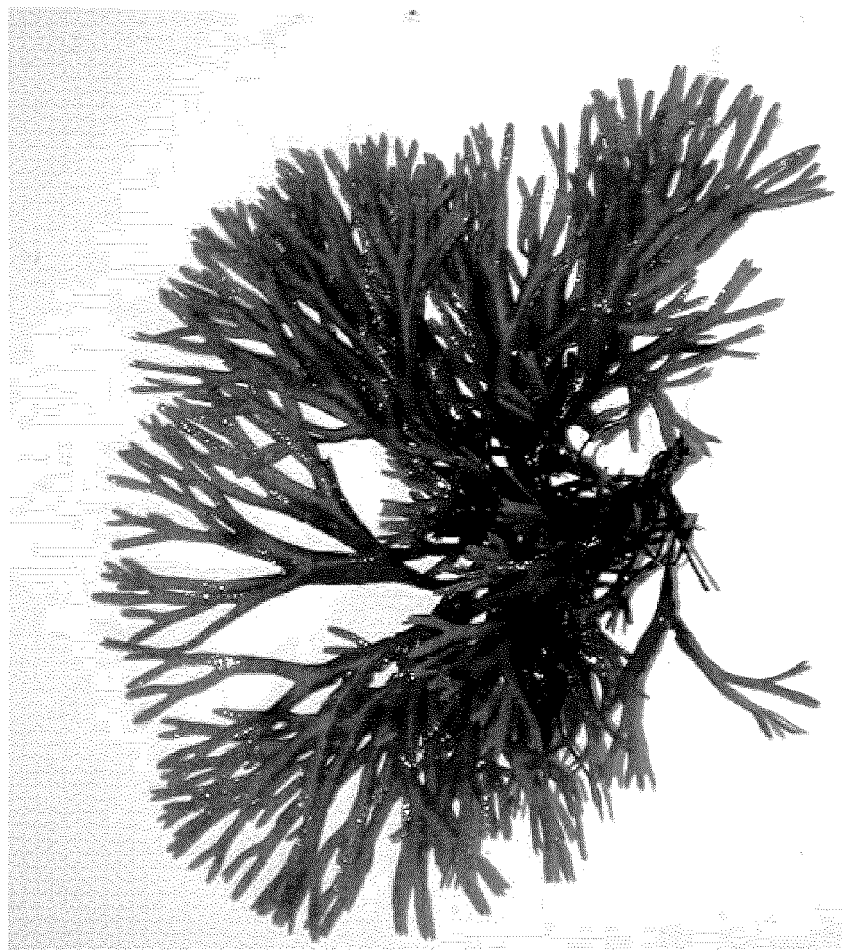
FIG. 1. Photograph of *Fucus distichus* seaweed.

FD: *Fucus distichus* seaweed.

Definitions

The term "about" as used herein refers to a margin of + or −10% of the number indicated. For sake of precision, the term about when used in conjunction with, for example: 90% means 90%+/−9% i.e. from 81% to 99%. More precisely, the term about refer to + or −5% of the number indicated, where for example: 90% means 90%+/−4.5% i.e. from 86.5% to 94.5%.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the terms "disease" and "disorder" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

"Mammal" includes humans, domestic animals such as farm animals (e.g. swine, cattle, sheep, goats, horses, rabbits), household pets (e.g. cats, dogs, rabbits, hamsters, ferrets), and non-domestic animals such as wildlife and the like.

The term "subject" or "patient" as used herein refers to an animal, preferably a mammal, and most preferably a human who is the recipient of the treatment, observation or experiment.

The term "extract" as used herein means a composition prepared by contacting solvent with seaweed material, produced following the procedures of the invention, which demonstrates inhibitory activity against one or more cancer cell line in vitro. In one aspect of the invention, an extract demonstrates inhibitory activity against cancer cell growth in vivo. As used herein, the term "extract" means an extract that is: crude, fractionated, sub-fractionated, separated, isolated, enriched or purified without being limited thereto.

The term "isolated" is used herein to indicate that the protein exists in a physical milieu distinct from that in which it occurs in nature. For example, the isolated molecule may be substantially isolated (for example enriched or purified) with respect to the complex cellular milieu in which it naturally occurs, such as in a crude/primary extract or secondary fractions. When the isolated molecule is enriched or purified, the absolute level of purity is not critical and those skilled in the art can readily determine appropriate levels of purity according to the use to which the material is to be put. In some circumstances, the isolated molecule forms part of a composition (for example a more or less crude extract containing many other substances) or buffer system, which may for example contain other components. In other circumstances, the isolated molecule may be purified to essential homogeneity, for example as determined spectrophotometrically, by NMR or by chromatography (for example LC-MS).

The term "primary" or "crude" means compounds or molecules that have not been entirely separated from the components of the original composition in which it was present. Therefore, the terms "separating", "purifying" or "isolating" refers to methods by which one or more components of the biological sample are removed from one or more other components of the sample.

The extracts described herein can be formulated as compositions by formulation with additives such as physiologically-acceptable excipients, physiologically-acceptable carriers, and physiologically-acceptable vehicles, or as cosmetic formulations with additives such as pharmaceutically- and/or dermatologically-acceptable excipients, carriers, and/or vehicles.

As used herein, the term "pharmaceutically-acceptable" refers being useful in preparing a pharmaceutical composition that is generally safe, non-toxic and neither biologically nor otherwise undesirable and includes being useful for vetenary use as well as human pharmaceutical use.

As used herein, the term "dermatologically-acceptable" refers to molecular entities and compositions that are physiologically tolerable when applied topically on the skin and do not typically produce an allergic or similar unwanted reaction, such as redness or swelling and the like, when administered to human. Preferably, as used herein, the term "cosmetically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carrier, particularly for topical formulations. Suitable cosmetically carriers are described in "Remington's Pharmaceutical Sciences" by E. W. Martin.

Detailed Description of Particular Aspects of the Invention

Solvent Extracts

With the aim of providing an alternative source of antimicrobial molecules, there is provided a crude solvent extract from the seaweed *Fucus distichus* (FD). Particularly, the crude extract is an organic or inorganic solvent extract. More particularly, the extract's solvent is water or alcohol; and even more particularly: aqueous ethanol.

Particularly, the crude extract is an 80% aqueous ethanol extract of FD. More particularly, the crude extract is a previously hexane-defatted extract.

More particularly, the extract is a solvent fraction of the primary extract. Most particularly, the fraction is obtained by a second extraction with a solvent such as: hexane, ethyl acetate, chloroform or water.

Extract Form

In accordance with a particular aspect of the present invention, the extract is in dried form or in solution.

Composition and/or Formulation

In accordance with a particular aspect of the invention, there is provided a composition comprising the FD extract as defined herein, in admixture with a physiologically—(i.e. pharmaceutically or dermatologically) acceptable carrier.

Thus, aspects of the present disclosure provide for a composition for topical treatment of skin disorders (including acne vulgaris), the composition comprising an anti-microbial agent comprising the FD extract as defined herein, optionally in admixture with: one or more synergistic agent selected from the group of: anti-acne actives, anti-microbial actives, anti-fungal actives, anti-inflammatory actives, exfoliating agents and mixtures thereof; and a physiologically-acceptable carrier. In one embodiment, the anti-microbial agent comprises the FD extract as defined herein effective for inhibiting *p. acne* in a physiologically-acceptable carrier. By way of example, the composition may comprise between 0.001% and 50% (w/w) active ingredients, and 50% to 99.999% (w/w) physiologically-acceptable carrier.

The compositions of the invention include those suitable for oral, nasal, mucosal, rectal, topical, buccal (e.g., sub-lingual), mucosal, intraperitoneal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound that is being used.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid or paste (such as gel, lotion, cream, ointment, etc.); or as an oil-in-water or water-in-oil emulsion. Such compositions may be prepared by any suitable method of pharmacy, which includes the step of bringing into association the active compound and a suitable carrier (which may contain one or more accessory ingredients as noted above).

Compositions suitable for buccal (sub-lingual) administration include lozenges comprising the active compound in a flavored base, usually sucrose and acacia or tragacanth; and pastilles comprising the compound in an inert base such as gelatin and glycerin or sucrose and acacia.

Compositions of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes that render the composition isotonic with the blood of the intended recipient. Aqueous and non-aqueous sterile suspensions may include suspending agents and thickening agents. The compositions may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described.

For example, in one aspect of the present invention, there is provided an injectable, stable, sterile composition comprising an active compound as described herein, or a salt or prodrug thereof, in a unit dosage form in a sealed container. The compound or salt is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent that is physiologically acceptable may be employed in sufficient quantity to emulsify the compound or salt in an aqueous carrier. One such useful emulsifying agent is phosphatidyl choline.

Compositions suitable for rectal administration are preferably presented as unit dose suppositories. These may be prepared by mixing the active compound with one or more conventional solid carriers, for example, cocoa butter, and then shaping the resulting mixture.

In an alternative embodiment, the present composition may be administered via topical administration.

Compositions suitable for topical application to the skin preferably take the form of an ointment, cream, salve, foam, lotion, paste, gel, spray, aerosol, or oil. Carriers that may be used include petroleum jelly, lanoline, polyethylene glycols, alcohols (e.g., ethanol, isopropanol, etc.), transdermal enhancers, and combinations of two or more thereof.

Alternatively, the present composition may be formulated in a microcrystalline form, in a liposomal preparation or as a wipe. The present composition may be formulated to be used as a cleanser or a toner. The present composition may be formulated to be used on the whole surface of a target skin area or for spot skin treatment. Formulations suitable for a desired route of administration are within the skill of one in the art.

Inactive Ingredients and Carriers

The composition of the present invention may comprise, in addition to the active agent, one or more inactive ingredient selected from the group consisting of: carriers or excipients, viscosity or building agents, thickening agents, gelling agents and preservative agents.

The pharmaceutical compositions of the present invention can be formulated based on their routes of administration using methods well known in the art. For example, a sterile injectable preparation can be prepared as a sterile injectable aqueous or oleaginous suspension using suitable dispersing or wetting agents and suspending agents. Suppositories for rectal administration can be prepared by mixing drugs with a suitable non-irritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHARMACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

The choice of a suitable physiologically-acceptable carrier will depend on the exact nature of the particular formulation desired, e.g. whether the present topical composition is to be formulated into a liquid solution, a suspension, an ointment, a film or a gel. The choice of a suitable physiologically-acceptable carrier will also depend on the route of administration. Preferably, the carrier is formulated to be suitable for topical administration.

In accordance with a particular embodiment, the inactive ingredient may be: a polyacrylate, carbopol 940, 934, 970, 974, acacia, alginic acid, bentonite, carboxymethylcellulose, ethylcellulose, gelatin, hydroxyethylcellulose, hydroxypropyl cellulose, magnesium aluminum silicate, methylcellulose, poloxamers, polyvinyl alcohol, sodium alginate, tragacanth, and xanthan gum or mixtures thereof.

In still another embodiment, preservatives like paraben and triethanolamine may be added to increase the stability of the composition.

In the case of a topical formulation in a gel form, the carrier may be selected from the group consisting of: purified water; ammonium acryloyldimethyltaurate; VP colopolymer; aloe vera; edetate disodium; allantoin; methylchloroisothiazolinone; methylisothiazolinone; and mixtures thereof.

Alternatively, the present composition may be formulated as an anti-bacterial soap or detergent, for preventive or hygienic purposes. Particularly, in one embodiment, the anti-microbial detergent comprises an extract of the present invention in combination with one or more additional cleaning composition components. The choice of additional components is within the skill of the artisan and includes conventional ingredients, including the exemplary non-limiting components set forth herein.

The detergent composition may be suitable for washing skin or mucus membranes (mouthwash, nose drops or rinse, etc.), or cleaning hard surfaces such as e.g. floors, tables, or dish wash.

Use and Method of Treatment

In accordance with an alternative aspect, the present invention provides the use of the extract as defined herein for inhibiting growth of microbial cells. Particularly, there is provided the use of the extract as defined herein for the manufacture of composition for treating a microbial infection in a mammal.

In accordance with an alternative aspect of the invention, there is provided the use of the composition as defined herein for the treatment of a microbial infection in a mammal.

In accordance with a particular aspect, the present invention provides a method of inhibiting a microbial cell growth comprising contacting said cell with a growth-inhibiting concentration of the extract as defined herein or the composition as defined herein.

More particularly, there is provided a method of treatment of a microbial infection in a mammal comprising administering a growth-inhibiting concentration of the composition as defined herein to said mammal.

In another aspect of the present disclosure, there is provided a method for the treatment of a skin disorder in a subject in need thereof, wherein the method comprises administering to the subject a therapeutically effective amount of a composition comprising an anti-microbial amount of the FD extract as defined herein in admixture with a physiologically-acceptable carrier. In one embodiment, the administering is topical, whereby the treatment is applied to a skin area affected by the bacterial infection. Compositions suitable for the present method are disclosed herein.

In another aspect of the present disclosure, there is provided a use or a method for the treatment of MRSA in a pet, particularly a dog, wherein the method comprises administering to the pet a therapeutically effective amount of a composition comprising an anti-microbial amount of the FD extract as defined herein in admixture with a pharmaceutically-acceptable carrier. In one embodiment, the administering is topical, whereby the treatment is applied to a skin area affected by the MRSA infection. Compositions suitable for the present method are disclosed herein.

In a further aspect of the present disclosure, there is provided use and a method for the treatment of *Staphylococcus pseudointermedius* (SP) or methicillin-resistant SP in a pet, particularly a dog, wherein the method comprises administering to the pet a therapeutically effective amount of a composition comprising an anti-microbial amount of the FD extract as defined herein in admixture with a pharmaceutically-acceptable carrier. In one embodiment, the administering is topical, whereby the treatment is applied to a skin area affected by the SP infection. Compositions suitable for the present use and method are disclosed herein.

In a further aspect of the present disclosure, there is provided use and a method for the treatment of *Staphylococcus intermedius* (SI) or methicillin-resistant SI in a farm animal, particularly a rabbit, wherein the method comprises administering to the rabbit a therapeutically effective amount of a composition comprising an anti-microbial amount of the FD extract as defined herein in admixture with a pharmaceutically-acceptable carrier.

In one embodiment, the administering is topical, whereby the treatment is applied to a skin area affected by the SI infection. Compositions suitable for the present use and method are disclosed herein.

Bacterial Infection

According to a further aspect, the microbial infection is a bacterial infection or an antibiotic-resistant bacterial infection. Particularly, the bacterial infection may be selected from the group consisting of: *Staphylococcus aureus*, methicillin-resistant *Staphylococcus aureus* (MRSA), *Staphylococcus epidermidis*, *Propionibacterium acnes*, *Staphylococcus intermedius* (SI) and methicillin-resistant *Staphylococcus intermedius* (MRSI), *Staphylococcus pseudintermedius* (SP) and methicillin-resistant *Staphylococcus pseudintermedius* (MRSP).

Subject

In accordance with another aspect, the mammal may be a human, a farm animal or a pet such as, for example, horses, rabbits, cats or dogs, particularly dogs.

Cosmetic Indications

The present invention also provides for a use or a method for alleviating acne-associated symptoms, the method comprises administering to a skin area affected by acne a therapeutically-effective amount of a composition comprising the FD extract directed against the organisms associated with acne and a physiologically-acceptable carrier, optionally in admixture with one of: anti-acne actives, anti-microbial actives, antifungal actives, anti-inflammatory actives, exfoliating agents and mixtures thereof. Compositions for alleviating acne-associated symptoms are disclosed herein.

Method of Extraction

In accordance with a further aspect of the invention, there is provided a method for obtaining an extract from *Fucus distichus* (FD) comprising the steps of:
a) mixing material from seaweed *Fucus distichus* with a solvent to obtain a solvent; material mixture; and
b) separating a solid fraction and a liquid fraction from said mixture, said liquid fraction forming said extract from said seaweed material.

Particularly, the solvent is organic or inorganic; more particularly: water or alcohol; and most particularly: aqueous ethanol. Still, most particularly, the solvent is 80% aqueous ethanol.

In accordance with an alternative aspect, the method of the invention further comprises a hexane-defatting step prior to step a).

In accordance with a particular aspect, the method further comprises the step of: c) fractionating the extract from step b) with a further solvent selected from the group consisting of: hexane, ethyl acetate, chloroform, water and mixtures thereof to obtain a liquid fraction.

Alternatively, the method further comprises a step of drying the liquid fraction to obtain a dried extract.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

This disclosure describes *Fucus distichus* harvesting, preparation of extracts, and testing for anti-microbial activity.

Example 1

Seaweed Collection and Identification

In September 2008, *Fucus distichus* (FD) was collected by hand from Bonne Bay, Newfoundland, Canada. Samples were placed in plastic sampling bags and transported to Applicant's premises in coolers of seawater. Upon arrival in the laboratory, the specimens were washed individually to remove epiphytic and extraneous matter (sand, mussels, isopods, etc.). Samples were then checked visually to ensure they were clean. If not, remaining matter was removed by hand with further washing. Seaweeds were blotted dry, weighed to the nearest gram (Plant wet weight) and shredded. The shredded material was transferred into Erlenmeyer flasks and frozen at −60° C. until the extracts were prepared.

A representative sample was also photographed (FIG. 1) and frozen at −20° C. for confirmation of species by Dr. Robert Hooper, a phycologist at Memorial University of Newfoundland.

Extract Preparation

Figure 5:
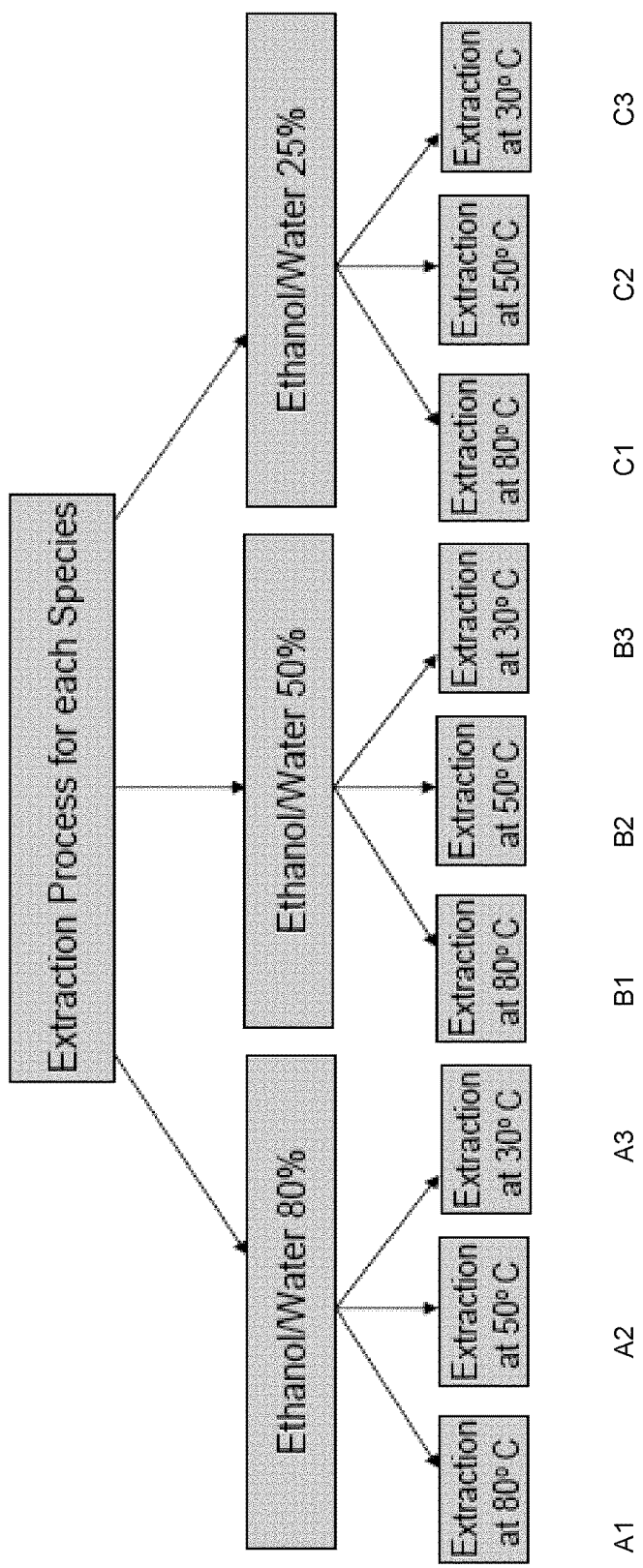
FIG. 5. Fractionation strategy for secondary fractionation of primary FD extracts.

Preparation of extract involved freeze drying and defatting samples, followed by extraction with 20% to 80% aqueous ethanol (FIG. 5).

Freeze-Drying

Seaweeds were freeze-dried prior to extraction. This step accounts for the differences in water content among seaweeds which may otherwise affect the solubility of bioactive components. Secondary plant metabolites are also more stable when stored in a dried form. Moreover, the large scale extraction of dried plant material may cause fewer problems than extracting fresh material. In order to preserve thermolabile compounds, low temperature conditions are used throughout the process of extraction.

Erlenmeyer flasks containing the shredded seaweeds, which had been frozen at −60° C., were placed on a freeze-dryer, and lyophilized for 72-96 h at $69 \times 10^{-3}$ mbar. The weight (g) of dry material was then recorded.

Defatting of Samples

The lipid fraction of seaweed is known to vary from 1 to 5% of the algal dry matter, which can be dominated by polyunsaturated fatty acids. Brown and red seaweeds are particularly rich in long chain polyunsaturated fatty acids such as eicosapentaenoic acid (n3, C20:5), while green seaweeds may possess a level of alpha linoleic acid (n3, C18:3). Since these polyunsaturated fatty acids are extremely susceptible to oxidation, they may result in lipid oxidation products during analysis. In order to eliminate the above oxidative processes that may have an effect on the results, samples were defatted prior to extraction.

Freeze dried seaweed samples were ground into a powder and defatted by blending the powder with hexane (1:5, w/v, 5 min) in a Waring blender at ambient temperature. Defatted samples were air-dried, vacuum packed in polyethylene pouches and kept at 4° C. until extraction.

Example 2

Crude Extraction

Different solvents or solvent systems can be used for the extraction. In general, ethanol is commonly used due to its lower toxicity compared to other solvents. Moreover, ethanol extracts have been demonstrated in many studies to have the highest antioxidant activity.

In the current study, bioactive compounds were extracted into 80% aqueous ethanol at 4° C. for 24 h. The solvent was then removed under a vacuum at 37° C. for 45 to 60 min and the resulting concentrated slurries were lyophilized for 72 to 96 h at −80° C. and $69 \times 10^{-3}$ mbar using a freeze dryer. Dry extracts were weighed and stored at −60° C. until preparation for screening.

Extraction Yield

Extraction yields were calculated and expressed as g of dry extract per kg of dry seaweed. The yield was 6.24%. Twenty five (25) mg of each extract was sent for anti-microbial screening assays.

Example 3. Primary Anti-Microbial Screening of *Fucus distichus* Extract

Experimental Conditions

The samples were tested to identify their capacity to inhibit the bacterial growth of *Staphylococcus epidermidis*, methicillin-resistant *Staphylococcus aureus* (MRSA), and *Propionibacterium acnes*. Table 1 enumerates the characteristics of the bacterial strains and antibiotics used as positive controls while Table 2 enumerates the optimal culture conditions.

TABLE 1

Summary of the bacterial strains characteristics, the selected antibiotics and the catalog numbers

| Bacteria | Characteristics | Supplier ATCC ® | Antibiotics |
|---|---|---|---|
| Staphylococcus epidermidis | Involved in nasal, urinary and cutaneous infections, Gram-positive | 12228 | Vancomycin |
| Methicillin-resistant Staphylococcus aureus (MRSA) | Involved in nosocomial and opportunistic infections, Gram-positive | 43300 | Chloramphenicol |
| Propionibacterium acnes | Linked to the skin condition, acne, Gran-positive | 6919 | Vancomycin |

TABLE 2

Summary of the experimental conditions

| Bacteria | Optimal liquid medium | Optimized growth conditions |
|---|---|---|
| Staphylococcus epidermidis | Mueller Hinton | Aerobic, 35-37° C., incubation 18-24 hrs |
| Methicillin-resistant Staphylococcus aureus (MRSA) | Mueller Hinton | Aerobic, 35-37° C., incubation 18-24 hrs |
| Propionibacterium acnes | Brain Hearth Infusion (BHI) + vit. K + Hémine | Aerobic, 35-37° C., incubation 48 hrs |

The sample (Table 3) and its solvent were tested simultaneously with antibiotic known to induce a strong inhibition of bacterial growth. An antibiotic is used to inhibit the growth of the bacterial strains. These antibiotics are used as positive controls identified by "INH" in the graphs. In addition, the extracts were tested in parallel with negative controls: the extracts solvent, labeled "Vehicle" and culture medium, labeled "Basal", respectively in the graphs. To ensure the reproducibility of the biological response, all the experimental conditions were tested in triplicate in 2 independent assays, represented by N=1 and N=2. The detection of the growth inhibition is noted by the turbidity measurement (measurement of absorbance at 625 nm) and by the metabolic activity (luminescent determination of ATP) expressed in "Relative Luminescence Unit" (RLU). With each test, an ATP standard curve is generated, by using the culture medium as solvent, in order to know the quantity of ATP measured in basal condition and using water as solvent in order to control the inter-assay detection variation.

TABLE 3

Summary of the characteristics of the extract #11

| Samples | Solvent | Concentration (mg/ml) | Final concentration with bacteria (µg/ml) |
|---|---|---|---|
| Extract #11 | DMSO 10% | 25 mg/0.5 ml | 50; 20; 8; 3.2 µg/ml |

A growth inhibition between 50 and 74% compared to the condition without extract, determined by vehicle (DMSO), is regarded as a significant response. While a growth inhibition superior to 75% is regarded as a highly significant answer. The comparison for the calculation of Z' is done between the condition of the inhibitor or the sample compared to the vehicle. When the Z' value approaches 1, the test is regarded as statistically significant. When the inhibition percentage is higher than 75% and the Z' value is nearly 1 the extract is considered very interesting.

Figure 2:
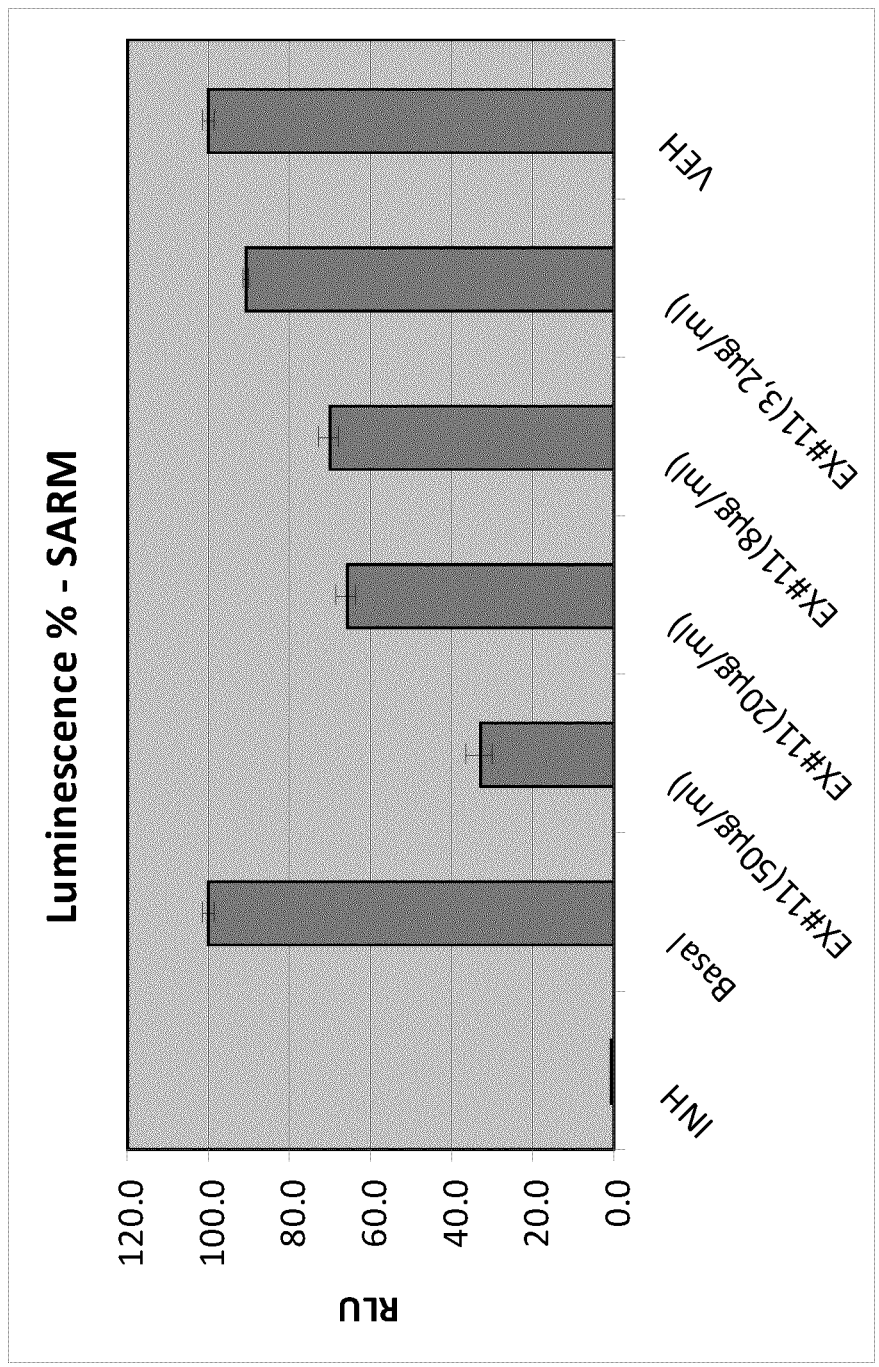
FIG. 2. Evaluation by luminescence of anti-microbial activity of a primary extract of FD against methycillin-resistant *Staphylococcus aureus* (MRSA).
Figure 3:
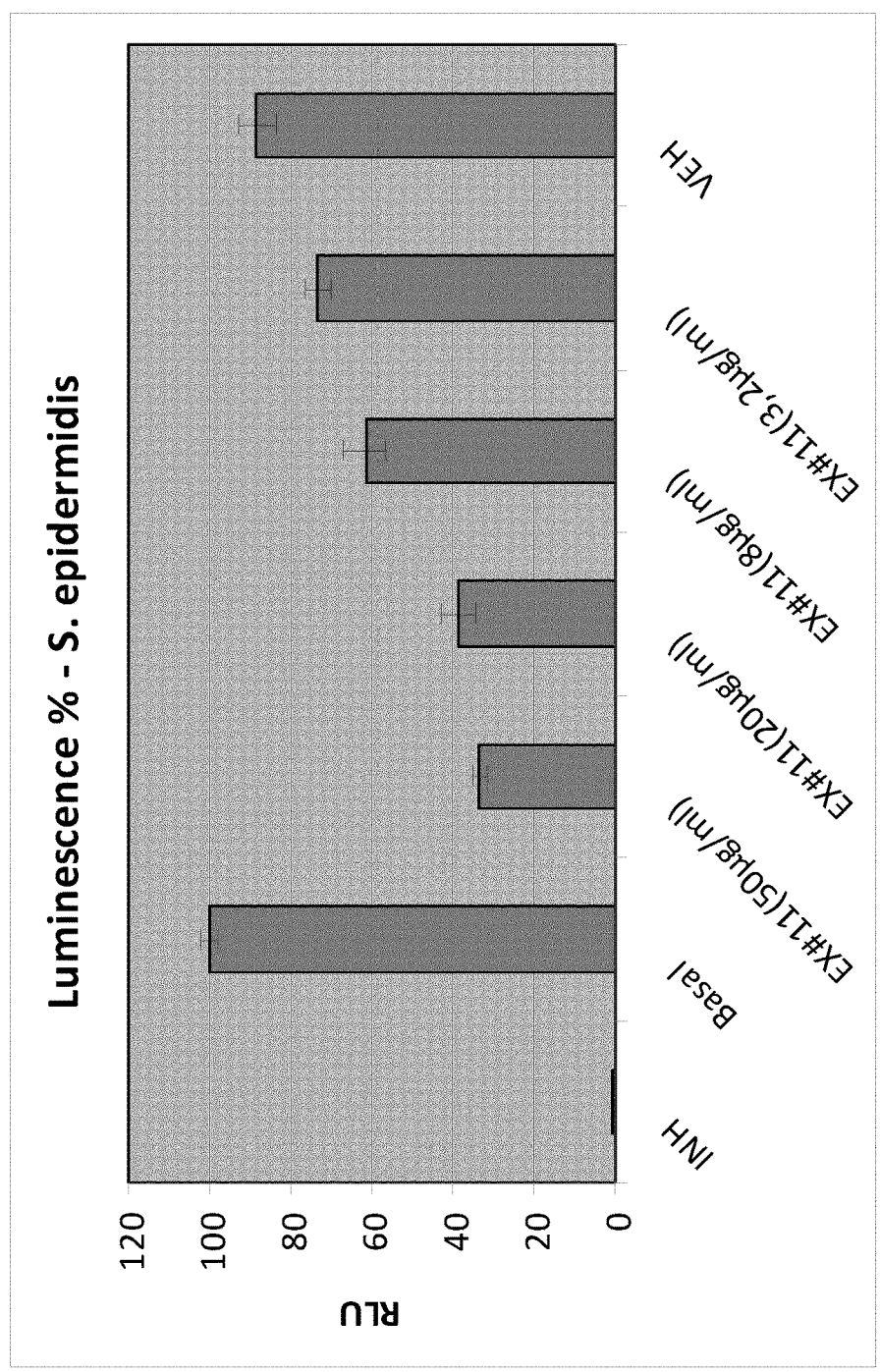
FIG. 3. Evaluation by luminescence of anti-microbial activity of a primary extract of FD against *Staphylococcus epidermidis*.
Figure 4:
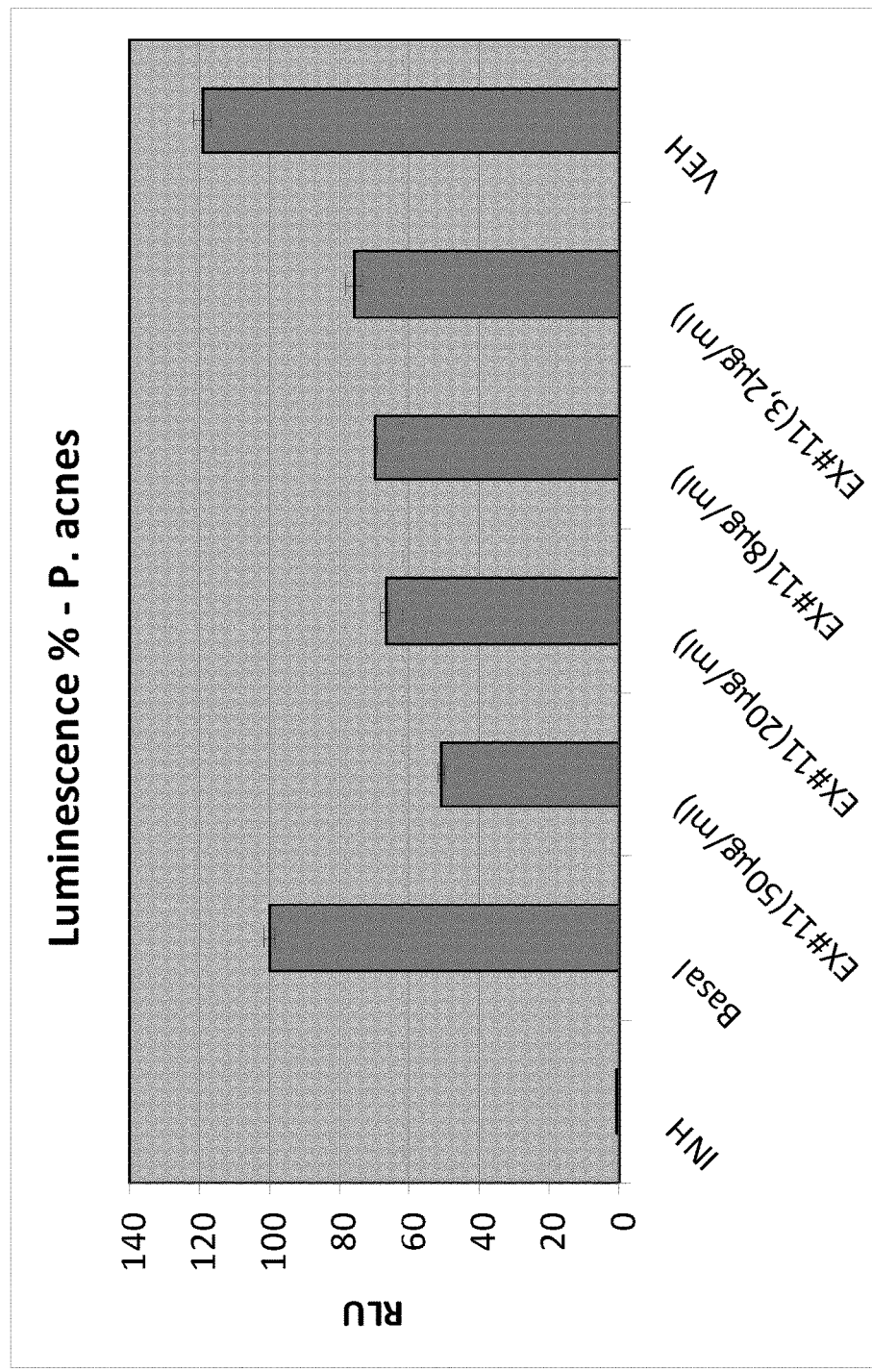
FIG. 4. Evaluation by luminescence of anti-microbial activity of a primary extract of FD against *Proprionibacterium acnes*.

The observation of a dose-dependent effect of an extract can also be interesting. Dose-dependent effect means that the effect changes proportionally when the dose of the extract is changed. An inhibition percentage between 50 and 74% for an extract in more than one strain can also be very interesting. For example, extract #11 (Fucus distichus, FD) is interesting because it has an effect on three different strains: methicillin-resistant Staphylococcus aureus (FIG. 2), Staphylococcus epidermidis (FIG. 3) and Propionibacterium acnes (FIG. 4).

The results from Table 4 (below) show that FD Extract #11 has interesting biological activity by inhibiting growth of methicillin-resistant Staphylococcus aureus (MRSA), Staphylococcus epidermidis and Propionibacterium acnes.

TABLE 4

Summary of anti-microbial activity of FD extract #11

| | | % inhibition | | | | Z' | | | |
|---|---|---|---|---|---|---|---|---|---|
| Extracts | Strains | 50 µg/ml | 20 µg/ml | 8 µg/ml | 3.2 µg/ml | 50 µg/ml | 20 µg/ml | 8 µg/ml | 3.2 µg/ml |
| 11 N = 1 | S. | 49 | 18 | 12 | NO | 0.27 | | N/A | |
| N = 2 | epidermidis | 60 | 53 | 26 | 12 | 0.61 | 0.28 | N/A | |
| 11 N = 1 | SARM | 62 | 42 | 25 | 10 | 0.66 | 0.16 | N/A | |
| N = 2 | | 67 | 34 | 30 | 10 | 0.60 | 0.37 | 0.25 | N/A |
| 11 N = 1 | P. acnes | 36 | 15 | NO | 11 | 0.69 | | N/A | |
| N = 2 | | 58 | 44 | 42 | 36 | 0.73 | 0.60 | 0.65 | 0.29 |

Legend: NO: No inhibition, Z' value: Statistical value.

It was therefore thought appropriate to carry out a bio-guided fractionation of a second FD extract (#47) in order to better characterize the bioactive molecules contained therein.

Example 5. Bio-Guided Fractionation of *Fucus distichus* Extract #47 and Evaluation of Antimicrobial Activity In this example, FD primary extract #47 (obtained by the same protocol as extract #11) underwent secondary fractionation by four different solvents. The antibacterial activity of all secondary fractions thereby generated were tested on *Propionibacterium acnes*, *Staphylococcus epidermidis* and methicillin-resistant *Staphylococcus aureus* (MRSA).

Fractionation and Screening

The secondary fractionation (liquid-liquid) of FD Extract #47 was performed according to the solvent in which the dry extract was best dissolved. After some preliminary tests, FD Extract #47 was found to be very soluble in $H_2O$. Secondary fractionation was therefore undertaken on an aqueous solution of FD Extract #47, using three solvents of different polarity: a) hexane (H), b) ethyl acetate (Ac), and c) chloroform (CL). The remaining molecules in the solubilisation solvent ($H_2O$) are recovered to constitute the fourth secondary fraction.

The screening results obtained for the secondary fractions of FD Extract #47 showed anti-microbial activity of the ethyl acetate fraction against MRSA (Table 5), and anti-microbial activity of the chloroform fraction against *S. epidermis* and *p. acnes*. These results demonstrate the effectiveness of the methodology of the bio-guided fractionation, which concentrates the active molecules and targets the biological effect. Moreover, we can conclude that at least some of the active molecules contained in FD Extract #47 are polar in nature.

TABLE 5

Summary of anti-microbial activity of primary FD extract #47 and secondary fractions

| | | MRSA | | | | | | | | S. epi | | | | | |
|---|---|---|---|---|---|---|---|---|---|---|---|---|---|---|---|
| | | 50 μg/ml | | 20 μg/ml | | 8 μg/ml | | 3.5 μg/ml | | 50 μg/ml | | 20 μg/ml | | 8 μg/ml | |
| Screening | Extract | % | Z' | % | Z' | % | Z' | % | Z' | % | Z' | % | Z' | % | Z' |
| Primary | 47 | 63 | 0.67 | 45 | 0.35 | 28 | 0.45 | 6 | NA | 38 | NA | 4 | NA | 6 | NA |
| | N = 1 | | | | | | | | | | | | | | |
| | N = 2 | 70 | 0.75 | 26 | 0.23 | 20 | NA | 12 | NA | 30 | NA | 48 | 0.5 | 11 | NA |
| Secondary | 47H11571 | 26 | 0.06 | 17 | NA | 10 | NA | NO | 2.45 | 10 | NA | 6 | NA | 3 | NA |
| | N = 1 | | | | | | | | | | | | | | |
| | N = 2 | 13 | NA | 18 | NA | 2 | NA | 0 | NA | 23 | 0.3 | 17 | 0.3 | 9 | NA |
| | 47AC11571 | 55 | 0.92 | 14 | NA | 6 | NA | NO | 1.8 | 34 | 0.3 | 14 | NA | 9 | NA |
| | N = 1 | | | | | | | | | | | | | | |
| | N = 2 | 49 | 0.57 | 10 | NA | 4 | NA | 5 | NA | 40 | 0.1 | 8 | NA | 1 | NA |
| | 47CL11571 | 28 | 0.38 | 16 | 0.48 | 11 | NA | NO | 2.38 | 30 | 0.2 | 59 | 0.7 | 26 | NA |
| | N = 1 | | | | | | | | | | | | | | |
| | N = 2 | 30 | 0.11 | 23 | 0.32 | 11 | NA | 9 | NA | 50 | 0.5 | 65 | 0.4 | 36 | 0.77 |
| | 47H₂O11571 | 28 | 0.59 | 8 | NA | NO | 23 | NO | 1.62 | 9 | NA | 7 | NA | 8 | NA |
| | N = 1 | | | | | | | | | | | | | | |
| | N = 2 | 15 | NA | 4 | NA | 9 | NA | 7 | NA | 14 | NA | 17 | NA | 2 | NA |

| | | S. epi | | P. acnes | | | | | | | |
|---|---|---|---|---|---|---|---|---|---|---|---|
| | | 3.5 μg/ml | | 50 μg/ml | | 20 μg/ml | | 8 μg/ml | | 3.5 μg/ml | |
| Screening | Extract | % | Z' | % | Z' | % | Z' | % | Z' | % | Z' |
| Primary | 47 | 6 | NA | 59 | 0.8 | 41 | 0.6 | 18 | NA | 32 | 0.6 |
| | N = 1 | | | | | | | | | | |
| | N = 2 | NO | 3.82 | 53 | 0 | 49 | NA | 25 | NA | 33 | NA |
| Secondary | 47H11571 | NO | 10.4 | 45 | 0.7 | 27 | 0.4 | 30 | 0.4 | 21 | 0.3 |
| | N = 1 | | | | | | | | | | |
| | N = 2 | NO | 11.4 | 57 | 0.5 | 41 | 0.6 | 31 | 0.4 | 26 | 0.3 |
| | 47AC11571 | 2 | NA | 28 | 0.5 | 24 | 0.5 | 19 | 0.2 | 25 | 0.3 |
| | N = 1 | | | | | | | | | | |
| | N = 2 | 4 | NA | 33 | 0.5 | 25 | 0.3 | 20 | NA | 22 | NA |
| | 47CL11571 | 5 | NA | 54 | 0.7 | 38 | 0.3 | 42 | 0.7 | 22 | 0.6 |
| | N = 1 | | | | | | | | | | |
| | N = 2 | 9 | NA | 60 | 0.5 | 53 | 0.7 | 47 | 0.4 | 28 | 0.3 |
| | 47H₂O11571 | 15.5 | | 5 | NA | 15 | NA | 15 | NA | 19 | 0.3 |
| | N = 1 | | | | | | | | | | |
| | N = 2 | 3 | NA | 10 | NA | 13 | NA | 14 | NA | 23 | 0.1 |

Example 6. Improving Bioactivity for Anti-Acne Related Activity Associated with FD Extracts The specific objective of these experiments was to optimize bioactivity of the extracts and identify the geographic localization of the most promising natural resource.

A collection program for FD was established for different geographical regions on the west coast of Newfoundland and Labrador (Table 6).

TABLE 6

Extraction yields

| Samples | Date Collected | Location | Extract (g dry weight) | Yield (g dry extract/g dry plant) |
|---|---|---|---|---|
| *Fucus Distichus* #79 | Oct. 6, 2014 | Bradore, Quebec (BasinIsland) | 7.29 | 10.40 |
| *Fucus Distichus* #87 | Oct. 9, 2013 | Salmon pt. Bonne Bay, NF | 4.35 | 6.21 |
| *Fucus Distichus* #85 | Oct. 10, 2013 | Wild Cove, Bonne Bay, NF | 6.19 | 8.78 |

Table 7 shows the anti-microbial activity of the three primary extracts obtained from different locations during the collection program in October 2013, prepared in accordance with the protocol presented in Example 1 (80% aqueous ethanol).

TABLE 7

Summary of anti-microbial activity of primary FD extracts #79, 87 and 85 collected from different locations

| Extract | Mass (mg) | MRSA 50 µg/ml % | Z, | 20 µg/ml % | Z' | 8 µg/ml % | Z' | S. epi 50 µg/ml % | Z' | 20 µg/ml % | Z' |
|---|---|---|---|---|---|---|---|---|---|---|---|
| FD79 N = 1 | 20 mg/ml | 72.66 | 0.662 | 12.86 | NA | 7.968 | NA | 35.2 | NA | 18 | NA |
| N = 2 | | 69.96 | 0.724 | 11.24 | NA | 2.494 | NA | 61.34 | 0.124 | 9.13 | NA |
| FD87 N = 1 | 20 mg/ml | 97.38 | 0.926 | 76.01 | 0.539 | 10.31 | NA | 98.3 | 0.912 | 13.74 | NA |
| N = 2 | | 98.69 | 0.859 | 74.47 | 0.702 | 5.164 | NA | 98.15 | 0.649 | 30.13 | NA |
| FD85 N = 1 | 20 mg/ml | 98.91 | 0.93 | 95.67 | 0.889 | 22.47 | NA | 98.99 | 0.912 | 71.49 | 0.505 |
| N = 2 | | 98.87 | 0.862 | 92.47 | 0.645 | 18.93 | NA | 98.8 | 0.661 | 83.79 | 0.29 |

| Extract | Mass (mg) | S. epi 8 µg/ml % | Z' | P. acnes 50 µg/ml % | Z' | 20 µg/ml % | Z' | 8 µg/ml % | Z' |
|---|---|---|---|---|---|---|---|---|---|
| FD79 N = 1 | 20 mg/ml | 2.467 | NA | NO | 2.89 | NO | 2.329 | 4.92 | 0 |
| N = 2 | | 7.951 | NA | 5.856 | NA | 6.323 | 0.099 | 14.3 | 0 |
| FD87 N = 1 | 20 mg/ml | 5.33 | NA | 7.896 | NA | NO | 3.646 | NO | 4.857 |
| N = 2 | | 5.157 | NA | 31.46 | 0.191 | NO | 4.046 | NO | 2.454 |
| FD85 N = 1 | 20 mg/ml | 17.43 | NA | 11.43 | NA | NO | 2.43 | NO | 6.231 |
| N = 2 | | NO | 37.95 | 28.92 | NA | 1.35 | NA | 8.051 | NA |

This was followed by investigating different extraction conditions to potentially optimise bioactivity of FD extract #87. Three different solvent ratios were used (ethanol/water at 80, 50, and 25%). Extraction was performed at 3 different temperatures (30, 50, and 80° C.) for each sample (see FIG. 5).

TABLE 8

Extraction conditions for secondary fractionation of FD primary extract #87

| Samples and extract ID | Solvent ratio (ethanol:water) | Temperature | Extract dry weight (g) | Yield (g dry extract/g dry seaweed) |
|---|---|---|---|---|
| FD 87 A1 | A | 1) 80° C. | 0.49 | 10.0 |
| A2 | 80% | 2) 50° C. | 0.44 | 8.0 |
| A3 | | 3) 30° C. | 0.19 | 4.0 |
| B1 | B | 1) 80° C. | 0.49 | 10.0 |
| B2 | 50% | 2) 50° C. | 0.61 | 12.0 |
| B3 | | 3) 30° C. | 0.61 | 12.0 |
| C1 | C | 1) 80° C. | 1.14 | 22.0 |
| C2 | 25% | 2) 50° C. | 0.64 | 12.0 |
| C3 | | 3) 30° C. | 0.45 | 10.0 |

Extraction yields were calculated for each extract. Yields ranged from 4.0 to 22.0, when expressed as g of dry extract per g of dry seaweed (Table 8). It was noticed that using 25% aqueous ethanol at 80° C. increased the yield.

Table 9 shows that all secondary fractions showed high anti-microbial activity (i.e. >75% inhibition) against MRSA, and *S. epidermis*, at a concentration of 50 µg/ml. However, the activity against *P. acnes* showed inconsistent results that may be due to contamination of the original extract or contamination of the bacterial culture.

To ascertain activity of FD extract on *P. acnes*, five (5) extracts were selected from Table 9 and were further evaluated for their anti-P-acnes activity at the following concentrations: 200; 100; 50; 25; 8 and 3.2 µg/ml. Table 10 shows that primary or secondary FD extracts possess anti-*P. acnes* activity, albeit at concentrations of 200 and 100 µg/ml.

TABLE 9

Summary of anti-microbial activity of secondary extracts from FD primary extract # 87

| | | MRSA | | | | | | S. epi | | |
| | | 50 µg/ml | | 20 µg/ml | | 8 µg/ml | | 50 µg/ml | | 20 µg/ml | |
| Extract | Mass (mg) | % | Z' | % | Z' | % | Z' | % | Z' | % | Z' |
|---|---|---|---|---|---|---|---|---|---|---|---|
| FD87B N = 1 | 20 mg/ml | 88.82 | 0.561 | 79.12 | 0.847 | 33.25 | 0.372 | 92.39 | 0.794 | 25.1 | 0.026 |
| N = 2 | | 89.14 | 0.863 | 82.86 | 0.836 | 26 | 0.677 | 98.72 | 0.908 | 13.27 | NA |
| FD87C N = 1 | 20 mg/ml | 89.47 | 0.703 | 81.38 | 0.729 | 29.7 | 0.268 | 98.63 | 0.94 | 19.86 | NA |
| N = 2 | | 95.04 | 0.928 | 79.12 | 0.763 | 27.82 | 0.425 | 88.41 | 0.579 | 16.97 | NA |
| FD87A1 N = 1 | 20 mg/ml | 84.98 | 0.64 | 53.78 | 0.502 | 26.89 | 0.308 | 41.98 | NA | 14.08 | NA |
| N = 2 | | 79.61 | 0.631 | 56.68 | 0.527 | 25.72 | 0.59 | 43.96 | NA | 0.244 | NA |
| FD87A2 N = 1 | 20mg/ml | 81.69 | 0.792 | 55.52 | 0.457 | 38.55 | 0.58 | 60.05 | 0.75 | 7.798 | NA |
| N = 2 | | 86.12 | 0.901 | 69.08 | 0.823 | 25.49 | 0.572 | 80.75 | 0.256 | 5.688 | NA |
| FD87A3 N = 1 | 20 mg/ml | 86.01 | 0.838 | 62.36 | 0.522 | 30.68 | 0.446 | 34.04 | NA | 3.737 | NA |
| N = 2 | | 84.45 | 0.779 | 64.94 | 0.799 | 23.85 | 0.375 | 80.78 | 0.42 | 1.503 | NA |
| FD87B1 N = 1 | 20 mg/ml | 87.84 | 0.606 | 63.88 | 0.635 | 24.72 | 0.033 | 82.38 | 0.413 | 2.079 | NA |
| N = 2 | | 81.66 | 0.898 | 66.79 | 0.424 | 15.34 | 0.12 | 84.45 | 0.471 | NO | 5.946 |
| FD87B2 N = 1 | 20 mg/ml | 88.69 | 0.828 | 79.99 | 0.694 | 27.69 | 0.104 | 80.04 | 0.755 | 11.94 | NA |
| N = 2 | | 84.06 | 0.646 | 74.52 | 0.604 | 20.69 | NA | 77.85 | NA | NO | 6.064 |
| FD87B3N N = 1 | 20 mg/ml | 85.11 | 0.841 | 28.72 | 0.533 | 27.7 | 0.092 | 82.1 | 0.556 | NO | 386.8 |
| N = 2 | | 84.35 | 0.648 | 72.14 | 0.789 | 17.48 | NA | 82.07 | 0.413 | NO | 6.428 |
| FD87C1 N = 1 | 20 mg/ml | 88.99 | 0.784 | 70.68 | 0.741 | 21.32 | NA | 92.47 | 0.786 | 11.11 | NA |
| N = 2 | | 92.39 | 0.864 | 77.99 | 0.845 | 15.85 | NA | 79.75 | 0.141 | NO | 5.149 |
| FD87C2 N = 1 | 20 mg/ml | 90.35 | 0.774 | 78.08 | 0.694 | 29.1 | 0.385 | 72.11 | NA | 10.9 | NA |
| N = 2 | | 91.21 | 0.757 | 68.65 | 0.199 | 14.61 | 0.214 | 93.14 | 0.62 | 6.218 | NA |
| FD87C3 N = 1 | 20 mg/ml | 95.26 | 0.853 | 73.53 | 0.382 | 23.74 | NA | 86.87 | 0.645 | 10.21 | NA |
| N = 2 | | 90.64 | 0.618 | 64.71 | NA | 9.575 | NA | 45.67 | NA | NO | 12.03 |

| | | S. epi | | P. acnes | | | | | |
| | | 8 µg/ml | | 50 µg/ml | | 20 µg/ml | | 8 µg/ml | |
| Extract | Mass (mg) | % | Z' | % | Z' | % | Z' | % | Z' |
|---|---|---|---|---|---|---|---|---|---|
| FD87B N = 1 | 20 mg/ml | 7.787 | NA | NO | 1.965 | NO | 2.784 | 2.733 | NA |
| N = 2 | | NO | 6.343 | NO | 26.3 | NO | 9.488 | NO | 46.98 |
| FD87C N = 1 | 20 mg/ml | 11.31 | NA | 7.354 | NA | 0.835 | NA | 11.28 | 0 |
| N = 2 | | NO | 4.704 | NO | 5.155 | NO | 3.819 | NO | 0 |
| FD87A1 N = 1 | 20 mg/ml | 8.02 | NA | 0.931 | NA | NO | 4.18 | 6.12 | NA |
| N = 2 | | NO | 7.937 | NO | 10.64 | NO | 29.44 | NO | 13.3 |
| FD87A2 N = 1 | 20 mg/ml | 3.418 | NA | 4.548 | NA | NO | 3.557 | 1.959 | NA |
| N = 2 | | 0.337 | NA | 11.87 | NA | 8.152 | NA | 6.886 | NA |
| FD87A3 N = 1 | 20 mg/ml | 0.826 | NA | NO | 19.74 | NO | 4.399 | 1.838 | NA |
| N = 2 | | 2.948 | NA | NO | 4.709 | 1.524 | NA | 1.17 | NA |
| FD87B1 N = 1 | 20 mg/ml | NO | 9.984 | NO | 3.674 | NO | 5.28 | 23 | 0.184 |
| N = 2 | | NO | 3.499 | NO | 2.638 | NO | 2.84 | NO | 3.253 |
| FD87B2 N = 1 | 20 mg/ml | 0.261 | NA | 3.89 | NA | NO | 10.88 | 7.544 | NA |
| N = 2 | | NO | 3.711 | 0.146 | NA | NO | 8.029 | NO | 4.023 |
| FD87B3N N = 1 | 20 mg/ml | NO | 5.978 | NO | 6.528 | NO | 4.566 | 1.065 | 0 |
| N = 2 | | NO | 3.552 | NO | 3.252 | NO | 2.72 | NO | 0 |
| FD87C1 N = 1 | 20 mg/ml | NO | 9.48 | 1.17 | NA | NO | 2.189 | NO | 4.701 |
| N = 2 | | NO | 5.039 | NO | 3.289 | NO | 2.357 | NO | 2.372 |
| FD87C2 N = 1 | 20 mg/ml | 0.738 | NA | NO | 93.36 | NO | 3.458 | 4.705 | NA |
| N = 2 | | NO | 2.146 | NO | 3.09 | NO | 2.471 | NO | 2.383 |

TABLE 9-continued

Summary of anti-microbial activity of secondary extracts from FD primary extract # 87

| | | | | | | | | | | |
|---|---|---|---|---|---|---|---|---|---|---|
| FD87C3 N = 1 | 20 mg/ml | NO | 16.29 | 5.218 | NA | NO | 2.526 | NO | 4.192 |
| N = 2 | | NO | 1.82 | NO | 2.564 | NO | 2.293 | NO | 2.181 |

TABLE 10

Summary of anti-*P. acnes* activity of five selected extracts

| | | *P. acnes* | | | | | | *P. acnes* | | | | | |
|---|---|---|---|---|---|---|---|---|---|---|---|---|---|
| | Mass | 200 µg/ml | | 100 µg/ml | | 50 µg/ml | | 200 µg/ml | | 100 µg/ml | | 50 µg/ml | |
| Extract | (mg) | % | Z' | % | Z' | % | Z' | % | Z' | % | Z' | % | Z' |
| FD78 N = 1 | 20 mg/ml | 25.12 | 0.305 | NO | 7.781 | NO | 2.285 | NO | 11.16 | NO | 5.583 | 4.053 | NA |
| N = 2 | | 37.17 | 0.469 | 6.959 | NA | 0.413 | NA | 2.461 | NA | NO | 6.135 | 5.692 | NA |
| FD87 N = 1 | 20 mg/ml | 50.42 | 0.783 | 60.02 | 0.578 | 23.55 | NA | NO | 6.515 | NO | 3.392 | NO | 16.21 |
| N = 2 | | 48.47 | 0.621 | 64.37 | 0.559 | 26.32 | 0.054 | 0.605 | NA | NO | 3.392 | NO | 10.89 |
| FD87A2 N = 1 | 20 mg/ml | 49.52 | 0.691 | 49.52 | 0.691 | 4.685 | NA | NO | 771.1 | NO | 6.039 | 8.276 | NA |
| N = 2 | | 46.46 | 0.511 | 55.4 | 0.64 | 7.84 | NA | 6.099 | NA | NO | 674.5 | 9.196 | NA |
| FD87B2 N = 1 | 20 mg/ml | 45.96 | 0.705 | 3.516 | NA | NO | 2.54 | NO | 10.84 | 5.189 | NA | 12.43 | NA |
| N = 2 | | 46.25 | 0.498 | 10.35 | NA | NO | 4.072 | NO | 7.747 | 2.513 | NA | 7.142 | NA |
| FD87C3 N = 1 | 20 mg/ml | 53.41 | 0.865 | 47.71 | 0.46 | 18.99 | NA | NO | 10.36 | 4.344 | NA | 17.62 | NA |
| N = 2 | | 58.25 | 0.674 | 43.71 | NA | 14.77 | NA | NO | 7.638 | NO | 2307 | 7.33 | NA |

Despite inconsistent results for *P. acnes*, it remains clear that *Fucus distichus*, whether as a primary extract or as secondary fractions, possesses highly interesting anti-microbial activity against nosocomial infections and acne.

Example 7. Evaluation of *Fucus distichus* Activity Against *Staphylococcus pseudintermedius*

The objective of this project was to study the growth kinetic of *Staphylococcus pseudintermedius* (ATCC® 49051™) and test the activities of two FD extracts: FD85 and FD87 (in 80% ethanol as defined in Example 2).

Figure 6:
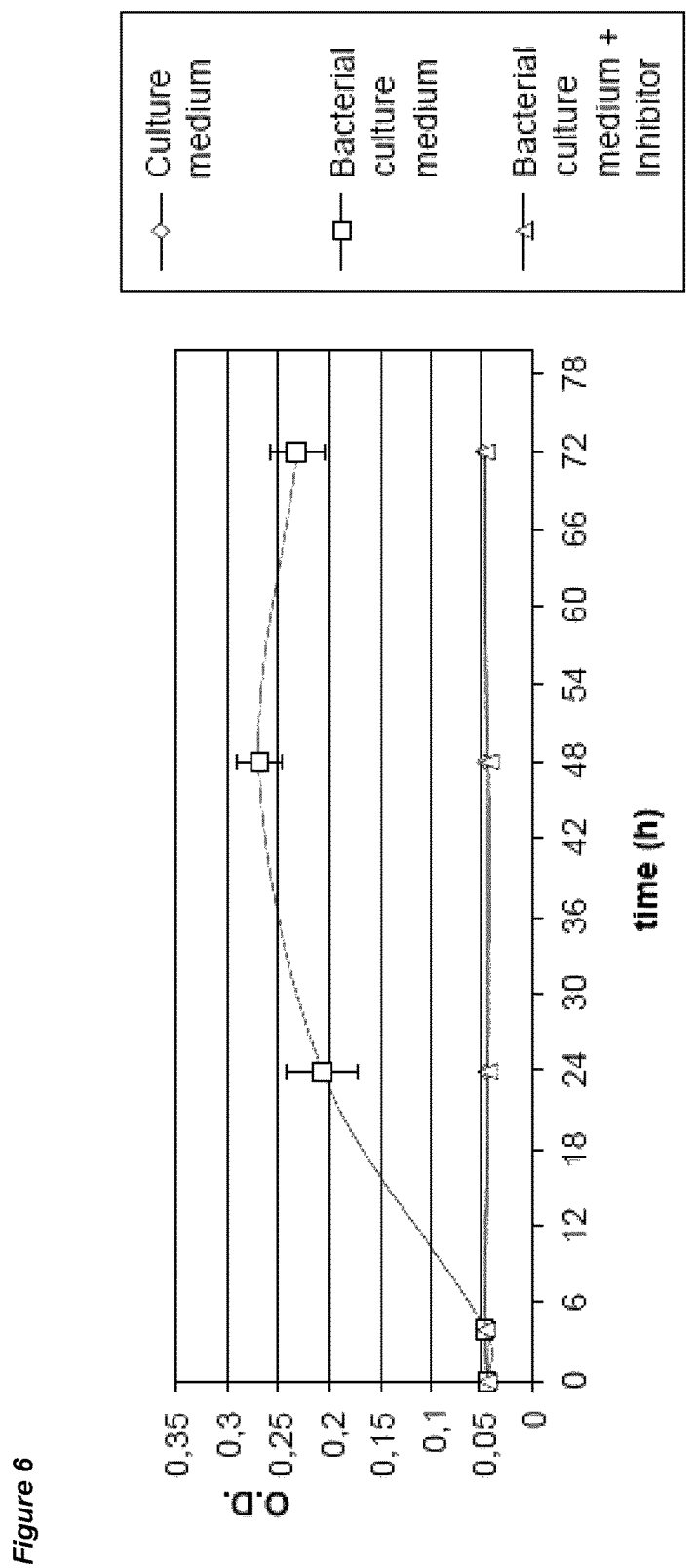
FIG. 6. Turbidimetry of *Staphylococcus pseudintermedius* according to time-points; bacterial suspension $10^3$ CFU-mL.
Figure 7:
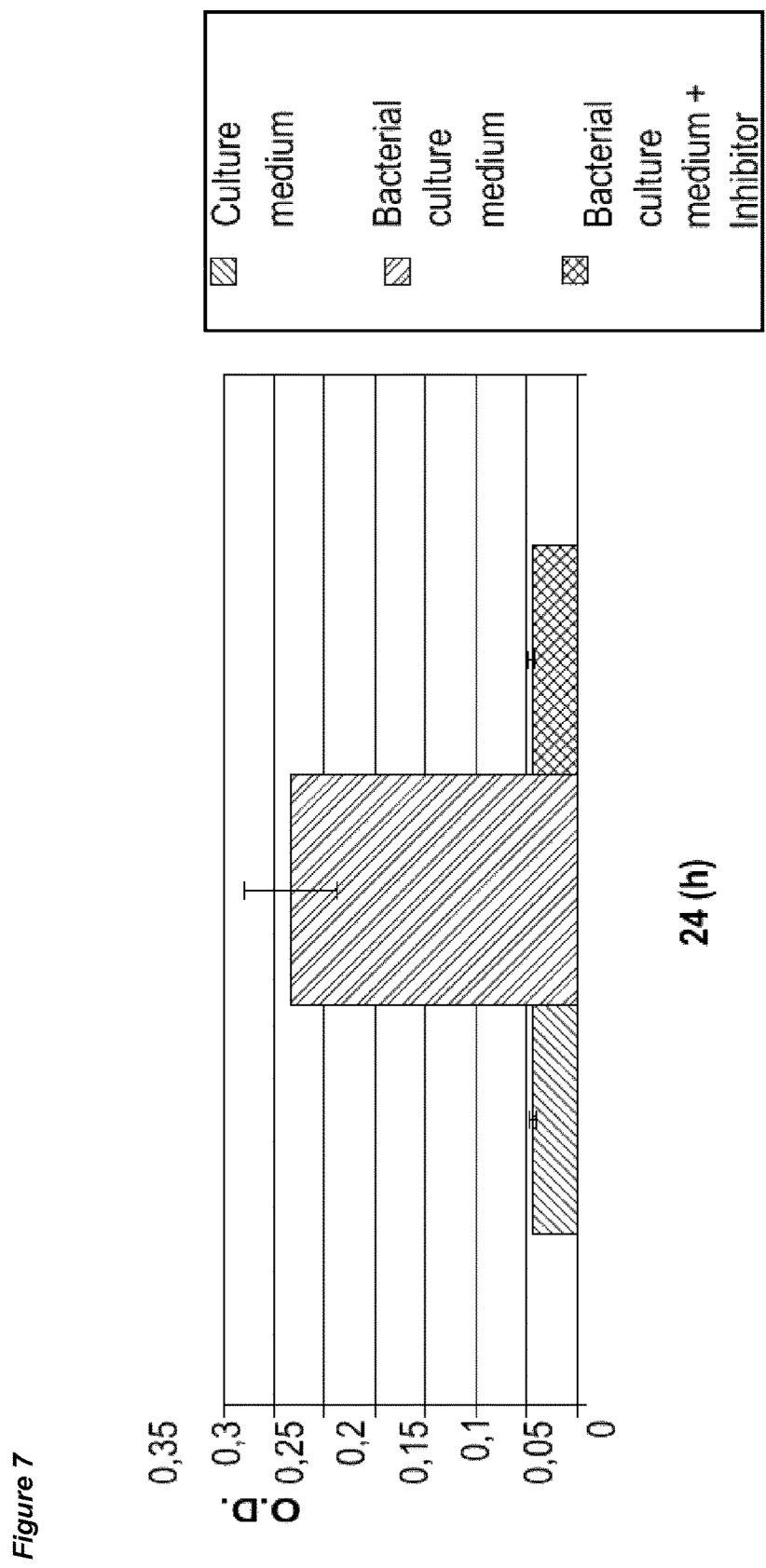
FIG. 7. Turbidimetry of *Staphylococcus pseudintermedius*; bacterial suspension $10^3$ CFU-mL in Mueller Hinton medium.
Figure 8:
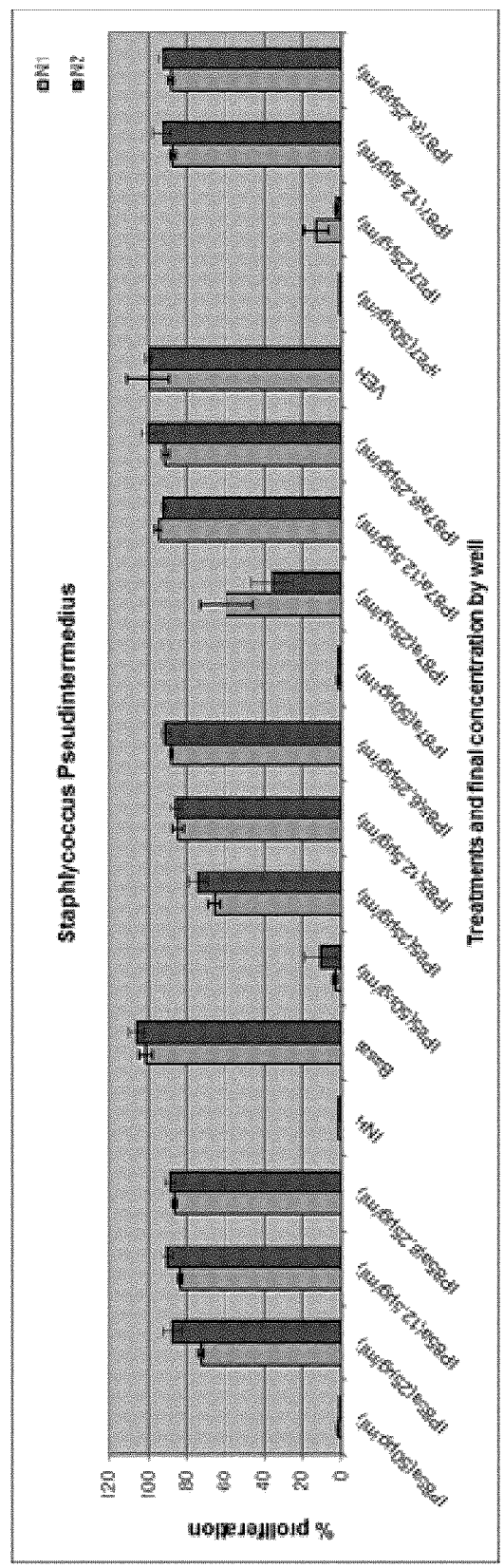
FIG. 8. Anti-microbial activity of a primary extracts of FD against *Staphylococcus pseudintermedius*.

Four samples (FD85 and FD87: in their original form, or FD85a and FD87a: previously pasteurized for 3 h) were assayed on antimicrobial screening at $10^3$ CFU/mL (see FIG. 6) in Mueller Hinton broth. The antibacterial activity was measured after 24 hours of incubation (see FIG. 7) with luminescence technology and is shown in Table 11 and FIG. 8.

Based on the results obtained, extracts FD85 and FD87 whether untreated or previously pasteurized (extracts "a") show high antimicrobial activity against *Staphylococcus Pseudintermedius* at 50 µg/mL.

Example 8. Clinical Trial of *Fucus distichus* Extracts Against *Staphylococcus Pseudintermedius* in Dogs Protocol Title: An open label study of Brown Seaweed (FD) Extract as a Topical Staph Infection Therapy for in dogs.

Purpose

Staph infections are common disease of dogs (mainly *S. pseudointermedius*). This study will investigate whether treatment with a topical gel (or drops) containing FD Seaweed extract is an effective therapy in twenty (20) otherwise healthy dogs with Staph Infections. The hypothesis is that

TABLE 11

Antimicrobial activity of FD extracts against SP (ATCC ® 49051 ™)

| | | | Mueller Hinton | | | | | | | |
|---|---|---|---|---|---|---|---|---|---|---|
| | | mass | 50 µg/ml | | 20 µg/ml | | 8.0 µg/ml | | 3.2 µg/ml | |
| Extract | | (mg) | % | Z' | % | Z' | % | Z' | % | Z' |
| FD85a | N = 1 | 20 mg/ml | 98.34 | 0.308 | | 0.105 | 16.64 | NA | 13.9 | NA |
| (Pasteurized) | N = 2 | | 98.81 | 0.889 | 12.9 | NA | 9.993 | NA | 11.82 | NA |
| FD85 | N = 1 | 17.55 mg/ml | 96.83 | 0.87 | | NA | 15.76 | NA | 12.44 | 0 |
| | N = 2 | | 89.49 | 0.347 | | NA | 14.61 | NA | 9.03 | NA |
| FD87a | N = 1 | 20 mg/ml | 98.32 | 0.917 | | NA | 4.977 | NA | 8.776 | NA |
| (Pasteurized) | N = 2 | | 98.65 | 0.872 | *64.36* | NA | 8.041 | NA | NO | 99.41 |
| FD87 | N = 1 | 13.65 mg/ml | 99.12 | 0.326 | 87.29 | NA | 13.13 | NA | 12.22 | NA |
| | N = 2 | | 99.26 | 0.894 | 97.33 | 0.84 | 7.251 | NA | 7.352 | NA |

Legend: NO = No inhibition, = INH25-50%, italics = INH 50-74%, and bold = INH 75-100% (a strong antimicrobial response)

treatment with a topical formulation containing FD extract will result in a significant improvement in Staph Infections after 14 days of treatment.

Primary Outcome Measures:
  Negative Culture for Staph Infection after 14 days of treatment (or less) with FD Seaweed extract.

Materials Under Test/Product Formulation

The topical preparation will consist of: 5 mg of FD seaweed extract per 100 mL (50 µg/mL) of usual gel or liquid formulation excipients (5% w/v of the total formulation).

Study Flow/Treatment Plan
  Visit 1
  Clinic Visit and Vet Assessment
  Medical History
  If deemed by Vet the dog as a Staph Infection then:
    A Culture will be performed to determine the type of Staph Infection
    The Infected Area will be prepped for Treatment
    A Topical Gel Application (One Daily) for 14 days or as otherwise directed by the vet of FD seaweed extract will be applied to the affected areas.
      If the infection is in the ear—Three (3) drops of FD seaweed extract will be used.
  Visit 2 (14 days or prior as deemed by Vet)
  Vet Assessment
  A Culture will be performed to determine if the of Staph Infection has cleared
  Adverse Event Query
  Visit 3 (1-2 weeks post treatment)
  Vet assessment to determine that the infection has not returned.

The invention claimed is:

1. A method for treating a bacterial infection in a mammal, said method comprising administering to said mammal a growth-inhibiting concentration of a composition comprising a solvent extract from a *Fucus distichus* (FD) seaweed, wherein said infection is from a bacteria selected from the group consisting of: *Staphylococcus pseudintermedius* (SP) and methicillin-resistant *Staphylococcus pseudintermedius* (MRSP).

2. The method of claim 1, wherein said mammal is a human or a pet.

3. The method of claim 1, wherein said solvent is aqueous ethanol.

4. The method of claim 3, wherein said solvent is between 25% and 80% aqueous ethanol.

5. The method of claim 1, wherein said seaweed is previously freeze-dried, grinded into powder form and defatted prior to solvent extraction.

6. The method of claim 5, wherein said powder is defatted with hexane.

7. The method of claim 1, said extract being further fractionated with a solvent selected from: organic or inorganic solvents.

8. The method of claim 7, wherein said fractionation solvent is selected from the group consisting of: hexane, ethyl acetate, chloroform, water, and mixtures thereof.

9. The method of claim 1, wherein said extract is an 80% ethanol extract of FD or a: hexane; ethyl acetate; chloroform; or water fraction from said 80% ethanol extract.

10. The method of claim 1, wherein said extract is in dried form or in solution.

11. The method of claim 2, wherein said pet is a dog.

* * * * *